United States Patent [19]

Blaine et al.

[11] Patent Number: 4,472,384

[45] Date of Patent: Sep. 18, 1984

[54] ANTIHYPERTENSIVE COMPOSITION

[75] Inventors: Edward H. Blaine, Chalfont; Charles S. Sweet, Telford, both of Pa.

[73] Assignee: Merck & Co., Inc., Rahway, N.J.

[21] Appl. No.: 504,639

[22] Filed: Jun. 15, 1983

[51] Int. Cl.$^3$ .............................................. A61K 37/00
[52] U.S. Cl. ................................................... 424/177
[58] Field of Search .................. 260/112.5 R; 424/177

[56] References Cited

U.S. PATENT DOCUMENTS

| | | | |
|---|---|---|---|
| 4,052,511 | 10/1977 | Cushman et al. | 424/274 |
| 4,129,571 | 12/1978 | Ondetti et al. | 260/326.2 |
| 4,154,960 | 5/1979 | Ondetti et al. | 562/426 |
| 4,225,609 | 9/1980 | Cragoe, Jr. et al. | 424/270 |
| 4,260,771 | 4/1981 | Cragoe, Jr. et al. | 548/187 |
| 4,374,829 | 2/1983 | Harris et al. | 424/177 |
| 4,379,792 | 4/1983 | Blaine | 424/270 |
| 4,390,703 | 6/1983 | Bock et al. | 548/187 |

*Primary Examiner*—Delbert R. Phillips
*Attorney, Agent, or Firm*—Salvatore C. Mitri; Mario A. Monaco

[57] ABSTRACT

A pharmaceutical composition is disclosed which comprises the combination of interphenylene 9-thia-11-oxo-12-aza prostanoic acid derivatives and carboxyalkyl dipeptide derivatives.

6 Claims, No Drawings

ANTIHYPERTENSIVE COMPOSITION

BACKGROUND OF THE INVENTION

The present invention is directed toward a pharmaceutical composition containing a renal vasodilator and antihypertensive agent; more particularly, an angiotensin converting enzyme inhibitor.

Antihypertensive agents are known (see e.g., U.S. Pat. Nos. 4,129,571, 4,154,960, 4,052,511, 4,374,829). A particularly preferred class of these compounds are those disclosed in U.S. Pat. No. 4,374,829.

Recently, a novel class of prostanoic acid type compounds having pharmacological activity have been disclosed (see e.g., U.S. Pat. Nos. 4,225,609 and 4,260,771). These compounds are racemic mixtures of interphenylene-9-thia-11-oxo-12-azaprostanoic acid and are especially effective renal vasodilators. More recently, a process was developed for separating these interphenylene racemates to obtain derivatives of interphenylene-9-thia-11-oxo-12-azaprostanoic acid as optically pure enantiomers (see commonly assigned U.S. application Ser. No. 276,117 filed June 22, 1981) and it is these optically pure enantiomers that are the preferred renal vasodilators in the composition of this invention.

It has been discovered that the combination of these preferred renal vasodilator compounds and the preferred antihypertensive agents produces a composition having enhanced pharmacological activity.

SUMMARY OF THE INVENTION

A pharmaceutical composition containing an interphenylene-9-thia-11-oxo-12-aza-prostanoic acid type renal vasodilator and a carboxyalkyl dipeptide antihypertensive agent.

DETAILED DESCRIPTION OF THE INVENTION

An embodiment of the invention is a pharmaceutical composition useful for treating hypertension which comprises:
(i) a renal vasodilator compound of the formula

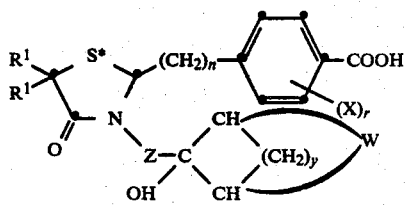

I wherein
the asterisk (*) marks the asymmetric carbon;
X is chlorine or methyl;
r is 0, 1 or 2;
n is 3 or 4;
$R^1$ is hydrogen, deuterium or methyl;
Z is ethylene, trimethylene, cis or trans-propenylene or propynylene;
y is 0, 1 or 2; and,
W is polymethylene of 2–6 carbon atoms; and,
(ii) an antihypertensive compound of the formula:

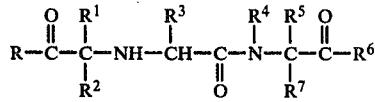

II wherein
R and $R_6$ are the same or different and are hydroxy,
lower alkoxy,
lower alkenoxy,
dilower alkylamino lower alkoxy (dimethylaminoethoxy),
acylamino lower alkoxy (acetylaminoethoxy),
acyloxy lower alkoxy (pivaloyloxymethoxy),
aryloxy, such as phenoxy,
arloweralkoxy, such as benzyloxy,
substituted aryloxy or substituted arloweralkoxy wherein the substituent is methyl,
halo or methoxy,
amino,
loweralkylamino,
diloweralkylamino,
hydroxyamino,
aryloweralkylamino such as benzylamino;
$R^1$ is
hydrogen,
alkyl of from 1 to 20 carbon atoms which include branched and cyclic and unsaturated (such as allyl) alkyl groups,
substituted loweralkyl wherein the substituent can be halo, hydroxy, lower alkoxy, aryloxy such as phenoxy, amino, diloweralkylamino, acylamino, such as acetamido and benzamido, arylamino, guanidino, imidazolyl, indolyl, mercapto, loweralkylthio, arylthio such as phenylthio, carboxy or carboxamido, carboloweralkoxy,
aryl such as phenyl or naphthyl,
substituted aryl such as phenyl wherein the substituent is lower alkyl, lower alkoxy or halo,
arloweralkyl, arloweralkenyl, heteroarlower alkyl or heteroarlower alkenyl such as benzyl, styryl of indolyl ethyl,
substituted arloweralkyl, substituted arloweralkenyl, substituted heteroarlower alkyl, or substituted heteroarlower alkenyl,
wherein the substituent(s) is halo, dihalo, lower alkyl, hydroxy, lower alkoxy, amino, aminomethyl, acylamino (acetylamino or benzoylamino) diloweralkylamino, loweralkylamino, carboxyl, haloloweralkyl, cyano or sulfonamido;
arloweralkyl or heteroarloweralkyl substituted on the alkyl portion by amino or acylamino (acetylamino or benzoylamino);
$R^2$ and $R^7$ are the same or different and are hydrogen or lower alkyl;
$R^3$ is hydrogen, lower alkyl, phenyl lower alkyl, aminomethyl phenyl lower alkyl, hydroxy phenyl lower alkyl, hydroxy lower alkyl, acylamino lower alkyl (such as benzoylamino lower alkyl, acetylamino lower alkyl), amino lower alkyl, dimethylamino lower alkyl, halo lower alkyl, quanidino lower alkyl, imidazolyl lower alkyl, indolyl lower alkyl, mercapto lower alkyl, lower alkyl thio lower alkyl;
$R^4$ is hydrogen or lower alkyl;

R⁵ is hydrogen, lower alkyl, phenyl, phenyl lower alkyl, hydroxy phenyl lower alkyl, hydroxy lower alkyl, amino lower alkyl, quanidino lower alkyl, imidazolyl lower alkyl, indolyl lower alkyl, mercapto lower alkyl or lower alkyl thio lower alkyl;

R⁴ and R⁵ may be connected together to form an alkylene bridge of from 2 to 4 carbon atoms, an alkylene bridge of from 2 to 3 carbon atoms and one sulfur atom, an alkylene bridge of from 3 to 4 carbon atoms containing a double bond or an alkylene bridge as above substituted with hydroxy, loweralkoxy, loweralkyl or diloweralkyl;

and the pharmaceutically acceptable salts thereof.

Examples of Formula I compounds are:

4-{3-[3-[2-(1-hydroxycyclohexyl)ethyl]-4-oxo-2-thiazolidinyl]propyl}benzoic acid;

4-{3-[3-[2-(1-hydroxycyclopentyl)ethyl]-4-oxo-2-thiazolidinyl]propyl}benzoic acid;

4-{3-[3-[2-(1-hydroxycycloheptyl)ethyl]-4-oxo-2-thiazolidinyl]propyl}benzoic acid;

4-{3-[3-[2-(1-hydroxy-4,4-dimethylcyclohexyl)ethyl)ethyl]-4-oxo-2-thiazolidinyl]propyl}-benzoic acid;

4-{3-[3-[2-(9-hydroxy-9-bicyclo[3.3.1]nonyl)ethyl]-4-oxo-2-thiazolidinyl]propyl}-benzoic acid;

4-{4-[3-[2-(1-hydroxycyclohexyl)ethyl]-4-oxo-2-thiazolidinyl]butyl}benzoic acid;

4-{3-[3-[3-(1-hydroxycyclohexyl)propyl]-4-oxo-2-thiazolidinyl]propyl}benzoic acid;

4-{3-[3-[3-(1-hydroxycyclohexyl)-trans-2-propenyl]-4-oxo-2-thiazolidinyl]propyl}benzoic acid;

4-{3-[3-[3-(1-hydroxycyclohexyl)-cis-2-propenyl]-4-oxo-2-thiazolidinyl]propyl}benzoic acid;

4-{3-[3-[3-(1-hydroxycyclohexyl)-2-propynyl]-4-oxo-2-thiazolidinyl]propyl}benzoic acid;

4-{3-[3-[2-(1-hydroxycyclohexyl)ethyl]-4-oxo-2-thiazolidinyl]propyl}-3-chlorobenzoic acid;

4-{3-[3-[2-(1-hydroxycyclohexyl)ethyl]-4-oxo-2-thiazolidinyl]propyl}-2-chlorobenzoic acid;

4-{3-[3-[2-(1-hydroxycyclohexyl)ethyl]-4-oxo-2-thiazolidinyl]propyl}-3-methylbenzoic acid;

4-{3-[3-[2-(1-hydroxycyclohexyl)ethyl]-5,5-dimethyl-4-oxo-2-thiazolidinyl]propyl}benzoic acid;

4-{3-[3-[2-(1-hydroxycyclohexyl)ethyl]-5,5-dideuterio-4-oxo-2-thiazolidinyl]propyl}benzoic acid and the like.

Examples of Formula II compounds are:

N-(1-carboxy-3-phenylpropyl)-L-alanyl-L-proline;

N-(1-ethoxycarbonyl-3-phenylpropyl)-L-alanyl-L-proline;

N-(1-ethoxycarbonyl-4-methylpentyl)-L-alanyl-L-proline;

N-(1-carboxy-5-aminopentyl)-L-alanyl-L-proline;

N-α-(1-carboxy-3-phenylpropyl)-L-lysyl-L-proline;

N-α-(1-ethoxycarbonyl-3-phenylpropyl)-L-lysyl-L-proline;

N-α-[1-carboxy-3-(3-indolyl)-propyl]-L-lysyl-L-proline;

N-α-[1-carboxy-3-(4-chlorophenyl)-propyl]-L-lysyl-L-proline;

N-α-[1-carboxy-2-phenylthioethyl]-L-lysyl-L-proline;

N-α-[1-carboxy-3-(4-chlorophenyl)-propyl]-L-lysyl-trans-4-methoxy-L-proline;

N-α-[1-carboxy-5-aminopentyl]-L-lysyl-L-proline;

N-α-(1-carboxy-3-phenylpropyl)-L-ornithyl-L-proline;

Ethyl N-(1-ethoxycarbonyl-3-phenylpropyl)-L-alanyl-L-prolinate hydrochloride;

N-[1-(ethoxycarbonyl)-3-(4-imidazolyl)propyl]-L-alanyl-L-proline.

N-[1-carboxy-3-(4-imidazolyl)propyl]-L-lysyl-L-proline;

N-(1(S)-carboxy-3-phenylpropyl)-L-alanyl-L-proline;

N-(1(S)-ethoxycarbonyl-3-phenylpropyl)-L-alanyl-L-proline;

N-(1(S)-ethoxycarbonyl-3-phenylpropyl)-L-alanyl-L-proline maleate salt;

N-α-(1(S)-carboxy-3-phenylpropyl)-L-lysyl-L-proline; and, ethyl N-(1(S)-ethoxycarbonyl-3-phenylpropyl)-L-alanyl-L-prolinate hydrochloride;

N-α-(1(S)-ethoxycarbonyl-3-phenylpropyl)-L-lysyl-L-proline.

The above described Formula II compounds, their use, and methods for their preparation are disclosed in U.S. Pat. No. 4,374,829 which is incorporated herein by reference.

The above-described Formula I compounds, their use and the method of preparation thereof are disclosed in U.S. Pat. No. 4,225,609 which is incorporated herein by reference.

The resolution of the Formula I diastereomeric compounds into their preferred optically pure enantiomers is disclosed in commonly assigned U.S. patent application Ser. No. 276,117 filed June 22, 1981 which is incorporated herein by reference.

This resolution process comprises (a) protecting the benzoic acid function of the Formula I compound e.g., by treating the acid with an alcohol or an alkyl halide in the presence of a catalyst to form an ester;

(b) treating the product from step (a) with an optically active esterifying agent in the presence of a catalyst and a base to form at least one separable diastereomeric ester;

(c) separating the diastereomeric esters into individual diastereoisomers; and (d) recovering the Formula I enantiomer from the individual corresponding diastereoisomers e.g., by hydrolysis in the presence of a catalyst in a suitable solvent.

The following flow sheet, illustrates the resolution process to obtain optically pure enantiomers of Formula I compounds:

FLOW SHEET OF EXAMPLE 1
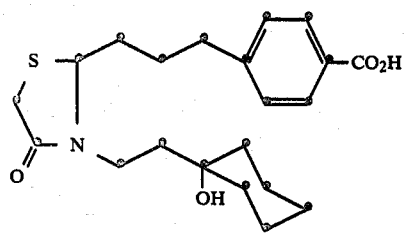
(±)-1 | Step A
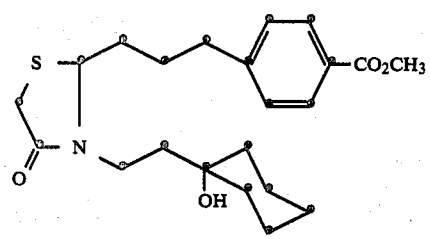
2 | Step B
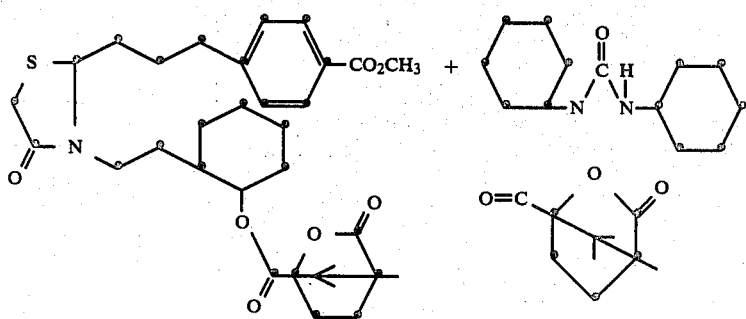
3     4¹
Step C

-continued
FLOW SHEET OF EXAMPLE 1

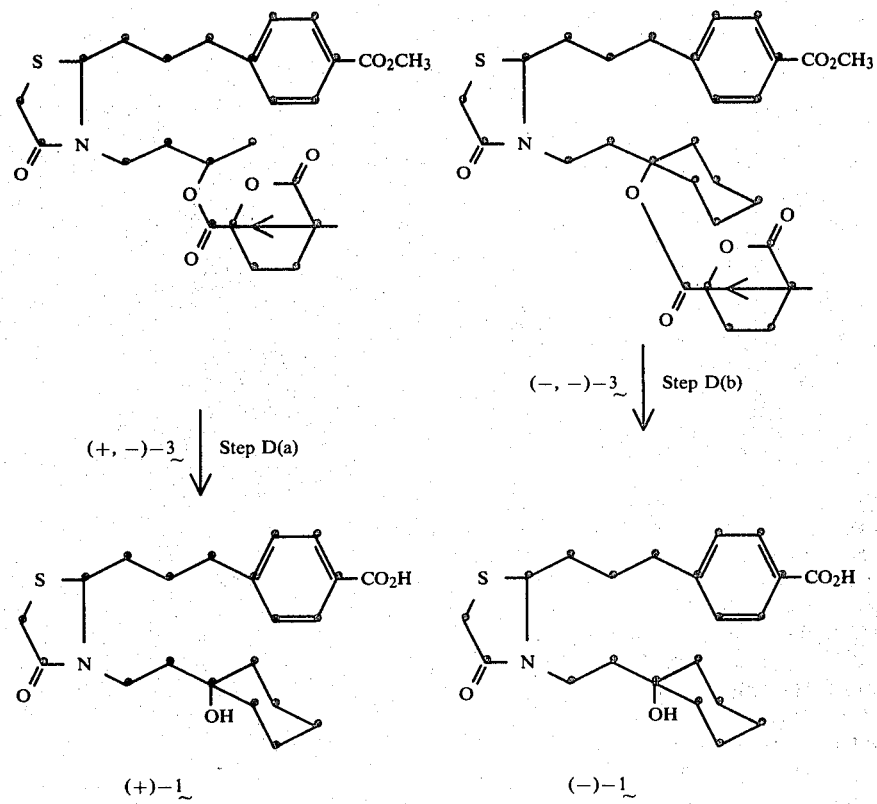

[1]This byproduct, acylurea 4, is separable by chromatography.

As outlined above in the flow scheme, the present process consists of four steps:

Step A—Protection of the benzoic acid

The benzoic acid is generally protected as an ester which can be removed easily via hydrolysis under mild conditions. Thus interphenylene-9-thia-11-oxo-12-aza-prostanoic acid is treated with an esterifying agent such as, for example, an alcohol or an alkyl halide in the presence of a catalyst to form a benzoate of the structural formula

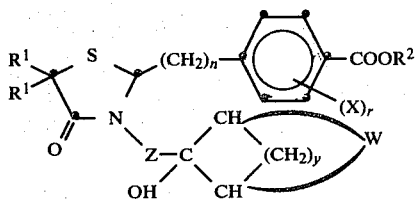

wherein $R^2$ is as described in, the following
(1) Description which summarizes the scope of esterification with an alcohol; and
(2) Description which summarizes the scope of esterification with a halide.

(1) Esterification of the Benzoic Acid with an Alcohol Alcohol ($R^2OH$)
 (a) $C_{1-5}$ alkanol wherein $R^2$ is methyl, ethyl, isopropyl, tertiary butyl; isoamyl or the like; or
 (b) phenyl-substituted methanol, e.g., benzyl alcohol, benzhydryl, or diphenylmethyl alcohol.

Catalyst under acidic conditions
 (a) sulfuric acid alone or in the presence of molecular sieves or arylsulfonic acids such as phenylsulfonic acid;
 (b) hydrochloric acid or hydrobromic acid; or
 (c) boron trifluoride-etherate.
Catalyst under neutral or basic conditions
 N,N'-dicyclohexylcarbodiimide;
 β-trichloromethyl-β-propiolactone;
 N,N'-carbonyldiimidazole;
 triphenylphosphine and diethylazodicarboxylate;
 1-methyl-2-chloropyridinium iodide; or
 6-chloro-1-p-chlorobenzenesulfonyloxybenzotriazole.

The preferred alcohol to be used is methanol or benzyl alcohol. The reaction is usually carried out in an excess amount of an alcohol in the presence of a catalyst. Under acidic conditions, the preferred catalysts are boron trifluoride etherate and sulfuric acid-molecular sieve. A typical procedure involves the refluxing of the benzoic acid, for example, compound 1, in an alcohol with a suitable catalyst under anhydrous conditions. The refluxing continues with or without stirring until a substantial amount of the acid is converted to the ester. Usually it requires about 0.5 to 48 hours, preferably about 2 to 6 hours to obtain optimal yield. Generally, reaction temperatures vary with the boiling point of the alcohol being used but can be adjusted to a range from about 25° C. to about 120° C. with the optional addition of an inert solvent, for example, diethyl ether, methylene chloride, benzene, toluene or xylene. The preferred temperatures are about 35° C. to about 80° C., since the thiazolidine ring of the compounds of this invention normally survives at such mild temperatures.

(2) Esterification with an Alkyl Halide (R³X)

As to esterification with alkylhalides, the benzoic acid is treated with a base to form a salt before subsequent treatment with an alkylhalide.
(a) C₁₋₅ alkylhalides wherein R³ is methyl, ethyl, n-propyl, n-butyl or isoamyl; and X is chloro, bromo or iodo; or
(b) benzyl chloride or the like.

Base for converting the benzoic acid to a salt
(a) a mineral base such as sodium hydroxide, potassium hydroxide, calcium hydroxide, sodium carbonate or potassium carbonate; or
(b) an organic base such as ammonium hydroxide, quaternary ammonium hydroxide, for example, tetramethylammonium hydroxide, tetraethylammonium hydroxide or phenyltrimethylammonium hydroxide.

The reaction is preferably carried out in a polar, aprotic solvent such as dimethylformamide (DMF), N,N-dimethylacetamide (DMAC), dimethylsulfoxide (DMSO), or hexamethylphosphoramide (HMPA). Other polar solvents may also be used. To minimize elimination, primary alkyl halides preferably methyl iodide or benzyl chloride are usually used and prolonged heating at high temperatures should be avoided. In most cases the reaction is conducted at about 0°–100° C. preferably at about 10°–40° C. For example, the reaction is stirred and maintained at about 25° C. until it is substantially complete, usually in about 1 to 48 hrs, preferably about 2 to about 10 hours under optimal conditions.

Step B—Formation of diastereoisomers

Esterification of the sterically hindered cyclohexyl hydroxyl group is accomplished by treating the product from Step A with an optically active acid generally in the presence of a base and a catalyst. Useful optically active acids, catalysts and bases are described below:

1. Optically active acids
   (+) or (−)-camphanic acid
   (+) or (−)-camphanyl anhydride
   (+) or (−)-camphorcarboxylic acid 2. Reagents for Esterification Involving Camphanic Acid or Camphorcarboxylic Acid In the Presence of An Organic Base
   Catalyst
   N,N'-dicyclohexylcarbodiimide (DCC)
   β-tri-chloromethyl-β-propiolactone
   N,N'-carbonyldiimidazole
   1-methyl-2-halopyridinium iodide
   (halo=F, Cl, Br or I)
   Base
   a trialkylamine (R₃N) wherein R is alkyl especially C₁₋₅alkyl such as methyl, ethyl or butyl
   pyridine
   4-dimethylaminopyridine
   2,4,6-collidine
   2,6-lutidine
   quinoline

Step C—Separation of the diastereoisomers

Fractional recrystallization is used to separate the diastereoisomers from Step (B) having the structural formula

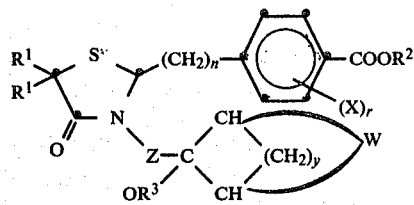

Typically, a suitable organic solvent is selected for successive recrystallization until an optically pure diastereoisomer is isolated. The solvents usually include water, acetonitrile, C₁₋₃ alkanol such as methanol or ethanol, acetone, methylacetate, ethylacetate, methylene chloride, ethyl ether, chloroform, dioxane, carbon tetrachloride, toluene, benzene, petroleum ether, n-pentane, n-hexane, cyclohexane or a mixture thereof. The preferred solvent for the camphanyl or camphorcarbonyl esters of the present invention is methylene chloride, chloroform, ethylacetate or a mixture thereof.

Step D—Hydrolysis

Hydrolysis of the highly hindered esters, for example, camphanyl esters, (−,−)-3 is difficult. A few representative hydrolysis procedures which are useful are described below:

TABLE VI

| | Hydrolysis | |
|---|---|---|
| | Catalyst | Solvent |
| (1) | sodium hydroxide (aqueous solution) | tetrahydrofuran-methanol-water |
| (2) | potassium hydroxide (aqueous solution) | tetrahydrofuran-methanol-water |
| (3) | potassium hydroxide (pellets) and dicyclohexyl-18-crown-6 (naked hydroxide ion) or sodium hydroxide pellets with other crown ethers | toluene or benzene |
| (4) | lithium tetrahydroboron | tetrahydrofuran, or hexamethyl phosphoramide (HMPA) or mixture thereof |

The hydrolysis is usually conducted at about 25° C. to about 120° C. depending on the solvent being used. For example, hydrolysis involving the naked hydroxyl ion (KOH-crown ether) is carried out preferably at about 40° C. to about 60° C. The reaction is continued with vigorous agitation until it is substantially complete, usually about 2 to 48 hours, preferably about 5 to about 24 hours.

The following example illustrates but does not limit the process of the present invention. The underlined numbers in the example identify the products as shown in the Flow Sheet above.

EXAMPLE 1

Resolution of Racemic 4{3-[3-[2-(1-hyroxycyclohexyl)ethyl]-4-oxo-2-thiazolidinyl]propyl}benzoic Acid Step A. Preparation of (±)-Methyl 4-{3-[3-[2-(1-Hydroxycyclohexyl)ethyl]-4-oxo-2-thiazolidinyl]propyl}benzoate (2)

To a freshly-prepared solution of (±)-4-{3-[3-[2-(1-hydroxycyclohexyl)ethyl]-4-oxo-2-thiazolidinyl]- propyl}benzoic acid (1) (10 g, 25.6 mmol) in dry N,N-dimethylformamide (86 ml) contained in a 250 ml round bottom flask is added finely-ground potassium carbonate (3.54 g, 25.6 mmol) followed by methyl iodide (1.6 ml, 25.6 mmol). The resulting suspension is protected from atmospheric moisture with a magnesium sulfate drying tube and is stirred at room temperature for 19.5 hours. The reaction mixture is poured into water (175 ml) contained in a separatory funnel and then is extracted with ether (3×40 ml). The organic extracts are combined, washed with saturated aqueous sodium bicarbonate (3×30 ml), dried over sodium sulfate and filtered. Evaporation (in vacuo) of the filtrate leaves the desired ester 2 as a pale yellow oil (10.55 g); tlc, $R_f$=0.4 (homogeneous, UV detection) on silica gel with ethyl acetate:hexane (7:3; v:v) as eluent; ir (2% solution in chloroform) 3400 (w), 1710 (s), 1600 (s) and 1280 (s) cm$^{-1}$.

Step B. Preparation of Methyl 4-{3-[3-[2-(1-(−)-camphanyloxy)cyclohexyl)-ethyl]-4-oxo-2-thiazolidinyl]-propyl}benzoate (3)

To a solution of (±)-methyl 4-{3-[3-[2-(1-hydroxycyclohexyl)ethyl]-4-oxo-2-thiazolidinyl]propyl}benzoate (2) (38.37 g, 94.6 mmol) in methylene chloride (189 ml) are added (−)-camphanic acid (20.64 g, 104.1 mmol) and 4-dimethylaminopyridine (5.77 g, 47.3 mmol). The resulting solution is cooled to 0° C. and treated with a solution of N,N'-dicyclohexylcarbodiimide (23.38 g, 113.52 mmol) in methylene chloride (180 ml) added slowly with stirring over 15 min. Thereby is obtained a heterogeneous mixture which is stirred at ambient temperature for 22 h. The reaction mixture is filtered to remove the insoluble solid (N,N'-dicyclohexylurea). The filtrate is washed with 0.2N hydrochloric acid (2×60 ml) and water (2×80 ml), dried over sodium sulfate and filtered. Evaporation (in vacuo) of the filtrate affords a brown, oily residue (semi-solid); tlc on silica gel with chloroform:methanol (98:2; v:v) indicates that the product 3, $R_f$=0.3, is accompanied by starting material 2 (ca. 5%) and traces of 4-dimethylaminopyridine.

The oily residue is "flash chromatographed" on silica gel (600 g, 230-400 mesh, E. Merck) using chloroform-methanol (98:2; v:v) as eluent and a flow rate sufficient to move the solvent front at of 1" per min. Thereby is eluted product 3 (ca. 55 g as a yellow solid) which is contaminated with N-((−)-camphanyl)-N,N'-dicyclohexylurea (4). Product 3 is used as such in Step C described below.

Step C. Separation of Mixture 3 Into Diastereomeric Components (−,−)-3 and (+,−)-3

(a) Isolation of (−,−)-3—Yellow solid 3 (ca. 55 g from Step B above) is triturated with ethyl acetate: hexane (1:1, v:v; 300 ml) at room temperature for 1 h to provide a heterogeneous mixture which is filtered. The collected, pale yellow solid (ca. 25 g of impure (−,−)-3) is recrystallized six times from ethyl acetate to afford pure diastereomer[1] (−,−)-3 as colorless crystals (8.85 g), mp 163°-164° C.; [α]$_D^{22}$= −47.3° (c 0.58, CHCl$_3$).
[1] Pmr analysis of (−,−)-3 and (+,−)-3 using the Europium shift reagent Eu(f0d)$_3$ shows that each of these materials is a single diastereomer.

(b) Isolation of (+,−)-3—The trituration filtrate from Step C (a) above is evaporated in vacuo to provide a residue[2] (ca. 24 g) consisting essentially of (+,−)-3 and byproduct 4. This residue is "flash chromatographed" in two separate 12 g portions as described below. A 12 g portion is applied in chloroform to a silica gel column (ca. 350 g, 230-400 mesh, E. Merck, 60 mm in diameter × 10" in length) which is eluted first with 30% ethyl acetate in hexane (2.4 L) at a flow rate sufficient to move the solvents front of 1" per min to remove the byproduct 4. Continued elution at the same flow rate with 40% ethyl acetate in hexane (1 L), 50% ethyl acetate in hexane (2 L) and 60% ethyl acetate in hexane (1 L) provides (+,−)-3. From the two "flash chromatographies" is obtained a pale yellow solid (15 g), [α]$_D^{22}$= +26.5° (c 0.57, CHCl$_3$). This solid is recrystallized from ethyl acetate to constant rotation. Thereby is obtained pure diastereomer (+,−)-3 as colorless crystals (10.55 g), mp 130°-132° C.; [α]$_D^{22}$= +37.2° (c 0.61, CHCl$_3$).
[2] This residue can be analyzed by tlc: $R_f$=0.12 for (+,−)-3 and $R_f$=0.36 for 4 on silica gel with ethyl acetate: hexane (3:7; v:v) elution followed by detection (dipping tlc plate in 5% sulfuric acid in ethanol and subsequent heating on a hot plate).
[3] See Footnote 1.

Step D. Hydrolysis of (+,−)-3 and (−,−)-3

(a) Preparation of (+)-4-{3-[3-[2-(1-Hydroxycyclohexyl)ethyl]-4-oxo-2-thiazolidinyl]-propyl}benzoic Acid To toluene (102 ml) contained in a 250 ml round bottom flask is added crushed solid potassium hydroxide (3.83 g, 68.3 mmol). The resulting heterogeneous mixture is heated at reflux until ca. 20 ml of distillate is collected[4] and then is cooled to room temperature. To the cooled heterogeneous mixture is added (+,−)-3 (4 g, 6.83 mmol) followed by dicyclohexyl-18-Crown-6 (12.72 g, 34.2 mmol). The resulting reaction mixture is protected from atmospheric moisture with a magnesium sulfate drying tube and is vigorously stirred and heated at 40° C. (oil bath) for 1 h. Then the drying tube is removed, water (80 ml) is added to the brown reaction mixture and stirring and heating at 40° C. are continued for 45 h. After cooling to room temperature, the reaction mixture is poured slowly into cold, excess N hydrochloric acid (200 ml) with vigorous stirring. The acidic,[5] aqueous mixture is transferred to a separatory funnel and the layers are allowed to separate. The aqueous layer (acidic phase) is extracted with chloroform (4×100 ml). The toluene and chloroform layers are combined, washed with water (2×100 ml), dried over sodium sulfate and filtered. Evaporation (in vacuo) of the filtrate leaves an oily residue which is triturated with ether at room temperature to afford an insoluble, colorless solid. The solid is collected, washed with ether and dried to give 2.04 g (76%) of (+)-1; tlc, $R_f$=0.26 (homogeneous, UV detection) with chloroform: methanol (9:1; v:v) on silica gel; identical by tlc to 1. Recrystallization from methanol affords pure enantiomer (+)-1 as colorless crystals (1.1 g), mp 139.5°-140.5° C.; [α]$_D^{22}$+70.0° (c 0.47, CHCl$_3$); ir (KBr pellet) 3270, 1690, 1640 and 1260 cm$^1$; pmr (CDCl$_3$) δ8.05 (2H, d), 7.28 (2H, d), 6.49 (2H, bs, OH and CO$_2$H), 4.75 (H, bm), 3.56 (2H, s), 2.68 (2H, t) and 1.60 (bc envelope).
[4] Azeotropic distillation ensures the removal of traces of moisture.
[5] The pH of this aqueous mixture should be checked with Congo red test paper; if not sufficiently acidic, additional 0.1N hydrochloric acid should be added prior to separation of the layers.

Anal. Calcd. for C$_{21}$H$_{29}$NO$_4$S: C, 64.42; H, 7.47; N, 3.58. Found: C, 64.57; H, 7.81; N, 3.51.

(b) Preparation of (−)-4-{3-[3-[2-(1-hydroxycyclohexyl)ethyl]-4-oxo-2-thiazolidinyl]propyl}benzoic Acid The hydrolysis of the pure diastereomer (−,−)-3 is carried out exactly as described above for (+,−)-3 in Step D (a). Thereby is obtained pure enantiomer (−)-1 as colorless crystals (1.24 g), mp 140°–141° C. (from CH$_3$OH); [α]$_D^{22}$ −68.7° (C 0.47, CHCl$_3$); tlc, ir and pmr data identical with those recorded for (+)-1.

Anal. Calcd. for C$_{21}$H$_{29}$NO$_4$S: C, 64.42; H, 7.47; N, 3.58: Found: C, 64.48; H, 7.72; N, 3.72.

Using substantially the same procedure as in Example 1 but substituting an equivalent amount of camphorcarboxylic acid for the camphanic acid, the corresponding camphor carbonyl esters are obtained and after separation and hydrolysis, comparable yields of the enantiomers of the azaprostanoic acid are obtained.

Substantially the same procedure as described in Example 1 was followed, but the following unresolved compounds were substituted for the racemic combinations used therein:

4-{3-[3-[2-(1-hydroxycyclohexyl)ethyl]-4-oxo-2-thiazolidinyl]propyl}benzoic acid;

4-{3-[3-[2-(1-hydroxycyclopentyl)ethyl]-4-oxo-2-thiazolidinyl]propyl}benzoic acid;

4-{3-[3-[2-(1-hydroxycycloheptyl)ethyl]-4-oxo-2-thiazolidinyl]propyl}benzoic acid;

4-{3-[3-[2-(1-hydroxy-4,4-dimethylcyclohexyl)ethyl]-4-oxo-2-thiazolidinyl]propyl}benzoic acid;

4-{3-[3-[2-(9-hydroxy-9-bicyclo[3.3.1]nonyl)ethyl]-4-oxo-2-thiazolidinyl]propyl}benzoic acid;

4-{4-[3-[2-(1-hydroxycyclohexyl)ethyl]-4-oxo-2-thiazolidinyl]butyl}benzoic acid;

4-{3-[3-[3-(1-hydroxycyclohexyl)propyl]-4-oxo-2-thiazolidinyl]propyl}benzoic acid;

4-{3-[3-[3-(1-hydroxycyclohexyl)-trans-2-propenyl]-4-oxo-2-thiazolidinyl]propyl}benzoic acid;

4-{3-[3-(1-hydroxycyclohexyl)-cis-2-propenyl]-4-oxo-2-thiazolidinyl]propyl}benzoic acid;

4-{3-[3-[3-(1-hydroxycyclohexyl)-2-propynyl]-4-oxo-2-thiazolidinyl]propyl}benzoic acid;

4-{3-[3-[2-(1-hydroxycyclohexyl)-ethyl]-4-oxo-2-thiazolidinyl]propyl}-3-chlorobenzoic acid;

4-{3-[3-[2-(1-hydroxycyclohexyl)-ethyl]-4-oxo-2-thiazolidinyl]propyl}-2-chlorobenzoic acid;

4-{3-[3-[2-(1-hydroxycyclohexyl)-ethyl]-4-oxo-2-thiazolidinyl]propyl}-3-methylbenzoic acid;

4-{3-[3-[2-(1-hydroxycyclohexyl)-ethyl]-5,5-dimethyl-4-oxo-2-thiazolidinyl]propyl}benzoic acid; or 4-{3-[3-[2-(1-hydroxycyclohexyl)-ethyl]-5,5-dideuterio-4-oxo-2-thiazolidinyl)propyl}benzoic acid.

From the foregoing unresolved compounds, there were obtained the following corresponding enantiomers:

(+) or (−)-4-{3-[3-[2-(1-hydroxycyclohexyl)ethyl]-4-oxo-2-thiazolidinyl]propyl}benzoic acid;

(+) or (−)-4-{3-[3-[2-(1-hydroxycyclopentyl)ethyl]-4-oxo-2-thiazolidinyl]propyl}benzoic acid;

(+) or (−)-4-{3-[3-[2-(1-hydroxycycloheptyl)ethyl]-4-oxo-2-thiazolidinyl]propyl}benzoic acid;

(+) or (−)-4-{3-[3-[2-(1-hydroxy-4,4-dimethylcyclohexyl)ethyl]-4-oxo-2-thiazolidinyl]propyl}benzoic acid;

(+) or (−)-4-{3-[3-[2-(9-hydroxy-9-bicyclo[3.3.1]nonyl)ethyl]-4-oxo-2-thiazolidinyl]propyl}benzoic acid;

(+) or (−)-4-{4-[3-[2-(1-hydroxycyclohexyl)ethyl]-4-oxo-2-thiazolidinyl]butyl}benzoic acid;

(+) or (−)-4-{3-[3-[3-(1-hydroxycyclohexyl)propyl]-4-oxo-2-thiazolidinyl]propyl}benzoic acid;

(+) or (−)-4-{3-[3-[3-(1-hydroxycyclohexyl)-trans-2-propenyl]-4-oxo-2-thiazolidinyl]propyl}benzoic acid;

(+) or (−)-4-{3-[3-[3-(1-hydroxycyclohexyl)-cis-2-propenyl]-4-oxo-2-thiazolidinyl]propyl}benzoic acid;

(+) or (−)-4-{3-[3-[3-(1-hydroxycyclohexyl)-2-propynyl]-4-oxo-2-thiazolidinyl]propyl}benzoic acid;

(+) or (−)-4-{3-[3-[2-(1-hydroxycyclohexyl)ethyl]-4-oxo-2-thiazolidinyl]propyl}-3-chlorobenzoic acid;

(+) or (−)-4-{3-[3-[2-(1-hydroxycyclohexyl)ethyl-4-oxo-2-thiazolidinyl]propyl}-2-chlorobenzoic acid;

(+) or (−)-4-{3-[3-[2-(1-hydroxycyclohexyl)ethyl]-4-oxo-2-thiazolidinyl]propyl}-3-methylbenzoic acid;

(+) or (−)-4-{3-[3-[2-(1-hydroxycyclohexyl)ethyl]-5,5-dimethyl-4-oxo-2-thiazolidinyl]propyl}benzoic acid; and (+) or (−)-4-{3-[3-[2-(1-hydroxycyclohexyl)ethyl]-5,5-dideuterio-4-oxo-2-thiazolidinyl]propyl}benzoic acid;

The composition of the invention can contain varying amounts of the Formula I (i) renal vasodilator and Formula II (ii) antihypertensive compounds. The weight ratio of (i):(ii) can range from about 1 to 25; preferably from about 1 to 10; more preferably from about 1 to 15. In addition to the active ingredients of (i) and (ii), the composition can also contain other conventional pharmaceutically acceptable compounding ingredients, as necessary or desired. Such ingredients are generally referred to as carriers or diluents. Conventional procedures for preparing such compositions in appropriate dosage forms can be utilized. Whatever the dosage form, it will contain a pharmaceutically effective amount of the present composition.

The present compositions can be administered orally or other than orally; e.g., parenterally, by insufflation, topically, rectally, etc.; using appropriate dosage forms; e.g., tablets, capsules, suspensions, solutions, and the like, for oral administration; suspension emulsions, and the like, for parenteral administration; and ointments, and the like, for topical administration.

Treatment dosage for human beings can be varied as necessary. Generally, daily dosages of the composition of the invention can range from about 550 to about 25 mg; preferably, from about 400 to about 60 mg; more preferably from about 200 to about 120 mg, using the appropriate dosage form and mode of administration.

The composition of this invention inhibits angiotensin converting enzyme and thus blocks conversion of the decapeptide angiotensin I to angiotensin II. Angiotensin II is a potent pressor substance. Thus blood-pressure lowering can result from inhibition of its biosynthesis especially in animals and humans whose hypertension is angiotensin II related. Furthermore, converting enzyme degrades the vasodepressor substance, bradykinin. Therefore, inhibitors of angiotensin converting enzyme may lower blood-pressure also by potentiation of bradykinin. Although the relative importance of these and other possible mechanisms remains to be established, inhibitors of angiotensin converting enzyme are effective antihypertensive agents in a variety of animal models and are useful clinically, for example, in many human patients with renovascular, malignant and essential hypertension. See, for example, D. W. Cushman et al., *Biochemistry* 16, 5484 (1977).

The evaluation of converting enzyme inhibitors is guided by in vitro enzyme inhibition assays. For example, a useful method is that of Y. Piquilloud, A. Reinharz and M. Roth, *Biochem. Biophys. Acta*, 206, 136 (1970) in which the hydrolysis of carbobenzyloxyphenylalanylhistidinylleucine is measured. In vivo evaluations may be made, for example, in normotensive rats challenged with angiotensin I by the technique of J. R. Weeks and J. A. Jones, *Proc. Soc. Exp. Biol. Med.*, 104, 646 (1960) or in a high renin rat model such as that of S. Koletsky et al., *Proc. Soc. Exp. Biol. Med.*, 125, 96 (1967).

Thus, the compositions of the invention are useful in treating hypertension. They are also of value in the management of acute and chronic congestive heart failure, in the treatment of secondary hyperaldosteronism, primary and secondary pulmonary hypertension, renal failure and renal vascular hypertension, and in the management of vascular disorders such as migraine or Raynaud's disease. The application of the compounds of this invention for these and similar disorders will be apparent to those skilled in the art.

In vivo testing of the composition of this invention in test animals (dogs) has demonstrated that this composition is pharmaceutically effective in lowering mean arterial pressure, reducing blood pressure, increasing heart rate, and increasing plasma renin activity.

The combination composition of the invention was administered to test animals (dogs) and the results obtained and the methods employed are described in Example 2 below.

tion of the 2 compounds at 9 a.m. and at 4:30 p.m. daily for 5 days. Blood pressure was measured immediately before and then 2 hours after the morning treatment.

Plasma samples for plasma rein activity (PRA) determinations were drawn on the first day of the treatment before the first dose (the control sample) and on the final day of that week 2 hours after the morning dosing. On each occasion, 5 ml of blood was withdrawn from the jugular vein and delivered into a chilled test tube containing ethylenediaminotetraacetate (EDTA). Plasma was separated by centrifugation at 4° C. and was stored at −20° C. until PRA was determined by use of the Clinical Assay Gamma Coat $^{125}$I radioimmunoassay kit. After each week of compound administration, 2 weeks in which no measurements were made and no treatments were given were allowed to assure that the animals had fully recovered. The protocol of 5 days of control observations and 5 days of treatment was then repeated until each dog had received each treatment once.

The data were subjected to analysis of variance for repeated measures. Differences between means were identified by application of the Newman-Keuls procedure. The results are set forth below in Tables I and II wherein the antihypertensive compound of the invention is identified as "A-H" and the renal vasodilator compound of the invention is identified as "RV".

TABLE I

Mean arterial pressures (MAP) and heart rates (HR) of hyptenive beagles*

| | Treatment | Control | Day of Treatment | | | | |
|---|---|---|---|---|---|---|---|
| | | | 1 | 2 | 3 | 4 | 5 |
| MAP (mm Hg) | A-H | 125 ± 6 | 119 ± 7 | 123 ± 7 | 120 ± 5 | 123 ± 5 | 122 ± 6 |
| | RV | 130 ± 4 | 125 ± 4 | 128 ± 4 | 124 ± 5 | 127 ± 4 | 141 ± 4 |
| | RV + A-H | 123 ± 3 | 120 ± 4 | 114 ± 7 | 113 ± 4 | 119 ± 6 | 118 ± 5 |
| HR (bpm) | A-H | 129 ± 9 | 135 ± 17 | 145 ± 6 | 133 ± 9 | 128 ± 7 | 129 ± 10 |
| | RV | 135 ± 9 | 136 ± 10 | 149 ± 5 | 137 ± 6 | 133 ± 4 | 132 ± 6 |
| | RV + A-H | 129 ± 9 | 123 ± 8 | 144 ± 6 | 144 ± 6 | 135 ± 7 | 140 ± 9 |

*Data presented as mean ± standard error of the mean.

EXAMPLE 2

Each of 6 female beagles was anesthetized and, under sterile conditions, one kidney was wrapped with cellophane. Two weeks later a contralateral nephrectomy was performed so that perinephritic hypertension developed. The surgical preparation of the dogs was completed at least one year prior to the administration of the combination composition of the invention. The dogs were trained to lie quietly on a table during puncture of a femoral artery with a 26 guage needle attached to a Micron pressure transducer. The output from the transducer was recorded on a 1-channel Gilson strip chart writer. The needle was left in the artery until a clear pulsatile pressure trace of at least 15 seconds duration was obtained. Heart rate was counted and mean arterial pressure (MAP) was calculated by adding the diastolic pressure to one-third of the pulse pressure. Five consecutive daily measurements were made in untreated hypertensive dogs. Subsequent statistical testing of the data by analysis of variance indicated that the blood pressure was constant over the course of the control week; an average of the 5 measurements for each dog was therefore used as the control MAP for that animal. During the following week, each dog received a gelatin capsule containing either 1 mg/kg of the antihypertensive compound of the invention, 0.2 mg/kg of the renal vasodilator compound of the invention or a combina-

TABLE II

Plasma renin activities (PRA) of hypertensive beagles before and after treatment.

| | PRA (mg/ml/hr) | |
|---|---|---|
| Treatment | Control | Day 5 |
| A-H | 0.99 ± 0.29 | 8.19 ± 0.68* |
| RV | 1.14 ± 0.44 | 5.58 ± 1.39* |
| RV + A-H | 0.58 ± 0.16 | 17.69 ± 2.98*+ |

Data presented as mean ± standard error of the mean
*p 0.01, control vs. day 5
+p 0.01, RV + A-H compared to A-H and to RV The data in Table I reveal that during the first 4 days of concurrent administration of the A-H compound and RV compound, MAP was significantly less in the treated dogs than in the untreated beagles. In contrast, administration of either compound alone produced no statistically significant effect on MAP when compared to controls. Statistical comparisons among the effects of the 3 treatments on a given day indicated that the A-H compound in combination with the RV compound lowered blood pressure to levels significantly less than those produced by either compound alone during the first 3 days and, on day 4, to a pressure less than the average of the dogs treated with the RV compound alone. Concurrent administration of the A-H compound with the RV compound to these mildly hypertensive beagles clearly reduced blood pressure to within the normotensive range, an effect which was not produced with either compound alone.

From Table I, it can also be seen that administration of the RV compound alone and in combination with the A-H compound significantly increased heart rate above the control levels on the first 3 days of compound administration. The A-H compound had no significant effect on pulse rate. The heart rates attained when the RV compound was administered singularly were significantly greater than those measured in dogs treated only with the A-H compound on the first 3 days of treatment. When the effects of the combination of the A-H and RV compounds were compared to those of A-H compound alone, significant differences were found on days 2 and 3 of treatment.

As shown in Table II, plasma renin activities (PRA) were similar at the end of each of the 3 control weeks. As expected all 3 treatments significantly increased PRA above the control levels. There was no significant difference between the renin level attained during treatment with the A-H comound and that measured during the RV compound treatment. The effects of the 2 compounds on renin release appeared to be additive since PRA during administration of the combination of the compounds was significantly higher than the activities measured during either treatment alone.

From the data shown in Tables I and II, it can be seen that mean arterial pressure (MAP) was significantly decreased only when the combination of the antihypertensive (A-H) and renal vasodilator (RV) compounds were administered. It can also be seen that administration of the renal vasodilator compound either alone or in combination with the antihypertensive compound significantly increased heart rate and also elevated plasma renin activities.

What is claimed is:

1. A pharmaceutical composition useful for treating hypertension comprising a pharmaceutically acceptable carrier; an antihypertensively effective amount of a renal vasodilator compound which is an optically pure enantiomer selected from the group:

(+) or (−)-4-{3-[3-[2-(1-hydroxycyclohexyl)ethyl]-4-oxo-2-thiazolidinyl]propyl}benzoic acid;

(+) or (−)-4-{3-[3-[2-(1-hydroxycyclopentyl)ethyl]-4-oxo-2-thiazolidinyl]propyl}benzoic acid;

(+) or (−)-4-{3-[3-[2-(1-hydroxycycloheptyl)ethyl]-4-oxo-2-thiazolidinyl]propyl}benzoic acid;

(+) or (−)-4-{3-[3-[2-(1-hydroxy-4,4-dimethylcyclohexyl)ethyl]-4-oxo-2-thiazolidinyl]propyl}benzoic acid;

(+) or (−)-4-{3-[3-[2-(9-hydroxy-9-bicyclo[3.3.1]nonyl)ethyl]-4-oxo-2-thiazolidinyl]propyl}benzoic acid;

(+) or (−)-4-{4-[3-[2-(1-hydroxycyclohexyl)ethyl]-4-oxo-2-thiazolidinyl]butyl}benzoic acid;

(+) or (−)-4-{3-[3-(1-hydroxycyclohexyl)propyl]-4-oxo-2-thiazolidinyl]propyl}benzoic acid;

(+) or (−)-4-{3-[3-[3-(1-hydroxycyclohexyl)-trans-2-propenyl]-4-oxo-2-thiazolidinyl]propyl}benzoic acid;

(+) or (−)-4-{3-[3-[3-(1-hydroxycyclohexyl)-cis-2-propenyl]-4-oxo-2-thiazolidinyl]propyl}benzoic acid;

(+) or (−)-4-{3-[3-[3-(1-hydroxycyclohexyl)-2-propynyl]-4-oxo-2-thiazolidinyl]propyl}benzoic acid;

(+) or (−)-4-{3-[3-[2-(1-hydroxycyclohexyl)ethyl]-4-oxo-2-thiazolidinyl]propyl}-3-chlorobenzoic acid;

(+) or (−)-4-{3-[3-[2-(1-hydroxycyclohexyl)ethyl-4-oxo-2-thiazolidinyl]propyl}-2-chlorobenzoic acid;

(+) or (−)-4-{3-[3-[2-(1-hydroxycyclohexyl)ethyl]-4-oxo-2-thiazolidinyl]propyl}-3-methylbenzoic acid;

(+) or (−)-4-{3-[3-[2-(1-hydroxycyclohexyl)ethyl]-5,5-dimethyl-4-oxo-2-thiazolidinyl]propyl}benzoic acid; and (+) or (−)-4-{3-[3-[2-(1-hydroxycyclohexyl)ethyl]-5,5-dideuterio-4-oxo-2-thiazolidinyl]propyl}benzoic acid; and, an antihypertensively effective amount of an antihypertensive compound selected from the group:

N-(1-carboxy-3-phenylpropyl)-L-alanyl-L-proline;
N-(1-ethoxycarbonyl-3-phenylpropyl)-L-alanyl-L-proline;
N-(1-ethoxycarbonyl-4-methylpentyl)-L-alanyl-L-proline;
N-(1-carboxy-5-aminopentyl)-L-alanyl-L-proline;
N-α-(1-carboxy-3-phenylpropyl)-L-lysyl-L-proline;
N-α-(1-ethoxycarbonyl-3-phenylpropyl)-L-lysyl-L-proline;
N-α-[1-carboxy-3-(3-indolyl)-propyl]-L-lysyl-L-proline;
N-α-[1-carboxy-3-(4-chlorophenyl)-propyl]-L-lysyl-L-proline;
N-α-[1-carboxy-2-phenylthioethyl]-L-lysyl-L-proline;
N-α-[1-carboxy-3-(4-chlorophenyl)-propyl]-L-lysyl-trans-4-methoxy-L-proline;
N-α-[1-carboxy-5-aminopentyl]-L-lysyl-L-proline;
N-α-(1-carboxy-3-phenylpropyl)-L-ornithyl-L-proline;
Ethyl N-(1-ethoxycarbonyl-3-phenylpropyl)-L-alanyl-L-prolinate hydrochloride;
N-[1-(ethoxycarbonyl)-3-(4-imidazolyl)propyl]-L-alanyl-L-proline;
N-[1-carboxy-3-(4-imidazolyl)propyl]-L-lysyl-L-proline;
N-(1(S)-carboxy-3-phenylpropyl)-L-alanyl-L-proline;
N-(1(S)-ethoxycarbonyl-3-phenylpropyl)-L-alanyl-L-proline;
N-(1(S)-ethoxycarbonyl-3-phenylpropyl)-L-alanyl-L-proline maleate salt;
N-α-(1(S)-carboxy-3-phenylpropyl)-L-lysyl-L-proline; and, ethyl N-(1(S)-ethoxycarbonyl-3-phenylpropyl)-L-alanyl-L-prolinate hydrochloride; and,
N-α-(1(S)-ethoxycarbonyl-3-phenylpropyl)-L-lysyl-L-proline.

2. The composition of claim 1 wherein said renal vasodilator compound is (+) or (−)-4-{3-[3-[2-(1-hydroxycyclohexyl)ethyl]-4-oxo-2-thiazolidinyl]propyl}benzoic acid; and, said antihypertensive compound is a member selected from the group consisting of:

N-(1(S)-ethoxycarbonyl-3-phenylpropyl)-L-alanyl-L-proline;
N(1(S)-carboxy-3-phenylpropyl)-L-alanyl-L-proline;
N-α-(1(S)-carboxy-3-phenylpropyl)-L-lysyl-L-proline; and, the maleate salts of said antihypertensive compounds.

3. The composition of claim 2 wherein said antihypertensive compound is N-(1(S)-ethoxycarbonyl-3-phenylpropyl)-L-alanyl-L-proline.

4. A method for treating hypertension comprising administering to a patient in need of such treatment an antihypertensively effective amount of a renal vasodilator compound as defined in claim 1 in combination with an antihypertensively effective amount of an antihypertensive compound as defined in claim 1.

5. The method of claim 4 wherein said renal vasodilator compound is (+) or (−)-4-{3-[3-[2-(1-hydroxycyclohexyl)ethyl]-4-oxo-2-thiazolidinyl]propyl}benzoic acid; and, said antihypertensive compound is a member selected from the group consisting of:
   N-(1(S)-ethoxycarbonyl-3-phenylpropyl)-L-alanyl-L-proline;
   N(1(S)-carboxy-3-phenylpropyl)-L-alanyl-L-proline;
   N-α-(1(S)-carboxy-3-phenylpropyl)-L-lysyl-L-proline; and, the maleate salts of said antihypertensive compounds.

6. The method of claim 5 wherein said antihypertensive compound is N-(1(S)-ethoxycarbonyl-3-phenylpropyl)-L-alanyl-L-proline.

* * * * *